United States Patent [19]

Hylton

[11] Patent Number: 4,518,799

[45] Date of Patent: May 21, 1985

[54] PROCESSES FOR THE PREPARATION OF HYDRATROPIC ACIDS

[75] Inventor: Thomas A. Hylton, Kalamazoo Township, Kalamazoo County, Mich.

[73] Assignee: The Upjohn Company, Kalamazoo, Mich.

[21] Appl. No.: 386,466

[22] Filed: Jun. 8, 1982

Related U.S. Application Data

[63] Continuation of Ser. No. 105,061, Dec. 19, 1979, abandoned.

[51] Int. Cl.$^3$ .............................................. C07C 51/15
[52] U.S. Cl. ................................... 562/423; 544/58.1; 544/171; 546/221; 546/238; 549/79; 549/454; 549/499; 548/444; 548/560; 548/563; 548/565; 548/572
[58] Field of Search ............... 544/58.1, 171; 546/221, 546/238; 549/29, 454, 499; 562/423; 548/444, 560, 563, 565, 572

[56] References Cited

U.S. PATENT DOCUMENTS

| | | | |
|---|---|---|---|
| 2,452,154 | 10/1948 | Ross | 260/593 |
| 3,483,248 | 12/1969 | Pattison | 562/492 |
| 3,651,106 | 3/1972 | Harrison | 562/423 |
| 3,784,705 | 1/1974 | Adams et al. | 424/317 |
| 3,959,364 | 5/1976 | Armitage | 562/496 |
| 3,987,057 | 10/1976 | Goddard | 260/326 |
| 3,992,459 | 11/1976 | Utne et al. | 260/649 |
| 4,144,397 | 3/1979 | Matthews | 562/496 |

FOREIGN PATENT DOCUMENTS 7603693 11/1976 Netherlands ................. 562/423

OTHER PUBLICATIONS

Kharasch, "Grignard Reactions of Nonmetalic Substance," pp. 909–947, (1954).
Kittila, "Dimethylformamide Chemical Uses," pp. 76–81, (1967).
Kuroda et al., Chem. Abstracts, 78, p. 43571q, (1973).
Wommack, J. B. et al., J. Het. Chem., 6, pp. 243–245, (1969).
Farady, L. et al., J. of Organomet. Chem., 28, pp. 159–165, (1971).
Farady, L. et al., J. of Organomet. Chem., 17, pp. 107–116, (1969).
March, Advanced Organic Chem.: Reactions, Mechanisms, & Structure, (McGraw-Hill), pp. 550–551, (1968).
Finkbeiner, H. L. et al., J. Org. Chem., 27, pp. 3395–3400, (1962).
Cadogan, J. I. G., J. Chem. Soc., (Notes), pp. 4257–4258, (1962).
Chem. Abstracts, 64, pp. 5005–5006, Boots Pure Drug, (1966).

*Primary Examiner*—Michael L. Shippen
*Attorney, Agent, or Firm*—William G. Jameson; Sidney B. Williams, Jr.

[57] ABSTRACT

Novel processes for making arylpropionic acids are described. One process comprises carboxylating particular Grignard compounds which are the products of a catalyzed reaction between corresponding arylmagnesium bromides and ethylene. Furthermore, the reaction making the particular Grignard compounds is itself novel. Also, an improved method is disclosed for making coupled aryl compounds useful as intermediates for making compounds having a pharmaceutical use. For example, particular biaryls may be used to make some of the Grignard compounds herein from which the arylpropionic acids are made. Finally, an improved bromination is disclosed giving high yields of 4-bromo-2-fluoroaniline, which is thereafter coupled with benzene, then used to make the arylmagnesium bromide reacted with ethylene to obtain the particular Grignard compound and subsequent desired arylpropionic acid, i.e. 2-(2-fluoro-4-biphenylyl)propionic acid.

12 Claims, No Drawings

PROCESSES FOR THE PREPARATION OF HYDRATROPIC ACIDS

SUMMARY OF THE INVENTION

This is a continuation of application Ser. No. 105,061, filed Dec. 19, 1979 now abandoned.

Novel processes for making arylpropionic acids are described. One process comprises carboxylating particular Grignard compounds which are the products of a catalyzed reaction between corresponding arylmagnesium bromides and ethylene. Furthermore, the reaction making the particular Grignard compounds is itself novel. Also, an improved method is disclosed for making coupled aryl compounds useful as intermediates for making compounds having a pharmaceutical use. For example, particular biaryls may be used to make some of the Grignard compounds herein from which the arylpropionic acids are made. Finally, an improved bromination is disclosed giving high yields of 4-bromo-2-fluoroaniline, which is thereafter coupled with benzene, then used to make the arylmagnesium bromide reacted with ethylene to obtain the particular Grignard compound and subsequent desired arylpropionic acid, i.e. 2-(2-fluoro-4-biphenylyl)propionic acid.

DETAILED DESCRIPTION OF THE INVENTION

This invention relates to a process for preparing a large number of 2-arylpropionic acids which are well known to have valuable therapeutic properties, such as, for example, anti-inflammatory activity.

Thus according to the invention there is provided a process for the preparation of a compound selected from the group consisting of

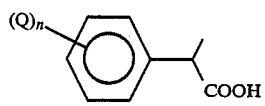
I in which n is an integer of from 1 to 4, inclusive, and Q is the same or different and is selected from the group consisting of aralkyl, cycloalkyl, alkyl substituted cycloalkyl, cycloalkenyl, aryl, alkoxy, aralkoxy, cycloalkoxy, aryloxy, alkylthio, aralkylthio, cycloalkylthio, arylthio, aryl(dialkoxy)methyl-, aryl(alkylene dioxy)methyl, N-alkyl-N-arylamino, trifluoromethyl, fluorine, chlorine, dialkylamino, substituted and unsubstituted pyridyl, piperidyl, furyl, N-alkyl-morpholino, N-alkyl-thiamorpholino, pyrrolinyl, pyrrolidinyl, pyrrolyl, thienyl, two Q groups taken together which form a heterocyclic ring or Q such that taken together with

is 9H-carbazol-3-yl or substituted naphthyl which comprises step (1) preparing a compound selected from the group consisting of

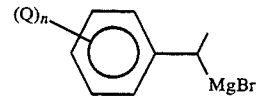
II by reacting a compound selected from the group consisting of

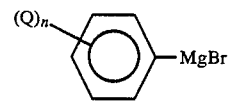
III with ethylene in the presence of a catalyst; and step (2) carboxylating the compound II prepared in step (1) to obtain I.

With respect to the Q substitution referred to above, the named moieties include examples as follows: aralkyl, e.g. benzyl; cycloalkyl, e.g. of 3 to 7 carbon atoms, and especially cyclohexyl; alkyl substituted cycloalkyl, e.g. wherein alkyl is methyl, ethyl, propyl, butyl (especially isobutyl), pentyl, branched hexyl and heptyl; cycloalkenyl, e.g. cyclohexenyl; aryl, e.g. phenyl and phenyl substituted with, for example 1 to 2 alkyl, alkoxy, or alkylthio, e.g. methylthio; fluorine or chlorine; alkoxy, e.g. methoxy, isopropoxy; aralkoxy, e.g. benzyloxy; cycloalkoxy, e.g. cyclohexyloxy; aryloxy, e.g. phenoxy and phenoxy substituted with, for example, 1 or 2 fluorine or chlorine atoms; alkylthio, e.g. methylthio, ethylthio, propylthio and n-butylthio; arylthio, e.g. phenylthio; aryl(dialkyloxy)methyl or aryl(alkylenedioxy)methyl; N-alkyl-N-arylamino in which the aryl is e.g. phenyl or phenyl substituted with, for example, one or more fluorine or chlorine atoms; two Q groups together form a heterocyclic ring, e.g. benzofuryl, indolyl or Q such that taken together with

is 9H-carbazol-3-yl, naphthyl, e.g., 6-methoxynaphth-2-yl.

Notably, step (1) above for preparing a compound selected from the group consisting of

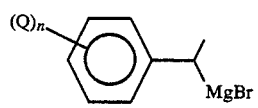
II wherein n and Q are as defined above is itself novel.

Preferred compounds I are those in which the

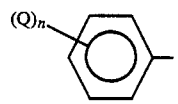

moiety is

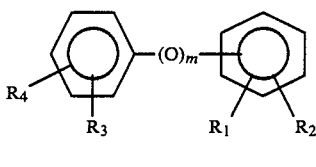

or

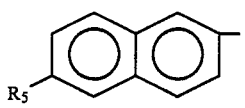

in which m is 0 or 1, and $R_1$ through $R_5$ may be the same or different and are selected from the group consisting of hydrogen, alkyl, cycloalkyl, phenyl, alkoxy, fluorine and chlorine. When m is 0, the moiety especially preferred is 2-fluoro-4-biphenylyl having the formula

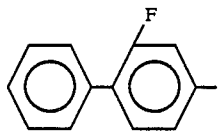

and when m is 1, the especially preferred moiety is 3-phenoxyphenyl having the formula

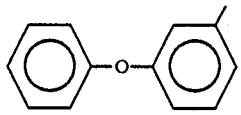

Preferred compounds I above also include those in which $R_5$ substituent is methoxy and fluoro.

As stated above step (1) is itself a reaction which insofar as is presently known, no one has previously used. L. Farady, et al. J. Organomet. Chem., 17, 107–116 (1969) reacts phenyl-, methyl- or ethylphenyl-, mesityl-, or naphthylmagnesium bromide with ethylene in the presence of anhydrous nickel chloride to obtain a corresponding α-phenyl-, methyl- or ethylphenyl-, mesityl-, or naphthyl-ethylmagnesium bromide. However, the process to make I or II by inserting an ethylene moiety into the substituted aryl magnesium bromides III of the above invention are not disclosed by this reference.

Another aspect of this invention is a process for the preparation of a compound having the formula

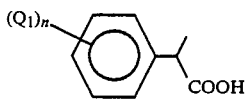

wherein n is an integer of from 1 to 4, inclusive, and $Q_1$ is the same or different and is a hydrocarbon selected from the group consisting of hydrogen, alkyl of from one to four carbons, inclusive, cycloalkyl, alkyl substituted cycloalkyl and cycloalkenyl which comprises step (A) preparing a compound selected from the group consisting of

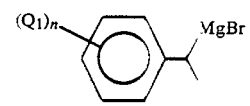

by reacting a compound selected from the group consisting of

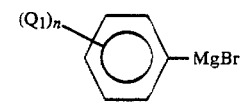

with ethylene in the presence of a catalyst in a solvent which comprises tetrahydrofuran, tetrahydropyran or 2-methyltetrahydrofuran and preferably a hydrocarbon cosolvent, and step (B) carboxylating the compound II″ prepared in step (A) to obtain I″.

The $Q_1$ substitution shown above includes examples of similarly named moieties as are disclosed for Q above.

Notably, step (A) above for preparing the compound having the formula

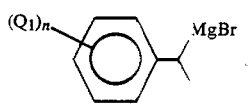

includes an improvement not known before the present invention through the use of particular ethereal solvents or mixtures thereof and preferably a hydrocarbon cosolvent to give unexpectedly higher yields and therefore is itself novel.

Examples of compounds I″ and II″ are those in which the substituent, or one of the substituents, $Q_1$ is in the 4-position, and is alkyl, e.g. isobutyl; cycloalkyl, e.g. cyclohexyl; or cyclohexenyl. Particularly preferred compounds are those in which $Q_1$ is isobutyl in the 4-position.

The L. Farady, et al. reference cited above discloses the ethylene addition to a phenyl or an alkyl substituted phenyl magnesium bromide in the presence of anhydrous nickel chloride, however, it is now discovered that an unexpectedly improved yield is obtained by the process in the present invention using particular ethereal solvents alone or preferably in combination with a hydrocarbon cosolvent and is therefore distinguished from the teachings of Farady et al.

The carboxylation of Grignard reagents as shown in both step (2) and step B of the above processes by carbonation to form carboxylic acids is well known in the art. Of particular interest as prior art for the present invention is Finkbeiner, et al., J. Org. Chem., 27, 3395 (1962), in which styrene is reacted with propylmagnesium bromide, in the presence of titanium tetrachloride, to form α-phenethylmagnesium bromide, which is reacted with $CO_2$ to obtain hydratropic acid. L. Farady, et al., J. of Organometallic Chemistry 28, 159 (1971) discuss a similar reaction with nickel chloride ($NiCl_2$). However, the particular reaction of ethylene with an aryl Grignard reagent III″ in the ethereal solvent or preferably with a hydrocarbon cosolvent of this invention is now shown.

Except as otherwise provided in subsequently disclosed novel preparations in this application for suitable aryl compounds from which arylmagnesium bromides can be made by known methods, the arylmagnesium bromides denoted as III and III'' are commercially available or may be prepared by a variety of methods described in the literature. However, the preparations in this application for the suitable precursor aryl compounds from which arylmagnesium bromides III and III'' can be made is not meant to be limiting and any known preparation therefore can also be used. For example, U.S. Pat. No. 2,452,154 discloses a bromination of organic compounds particularly useful to prepare starting materials III'' herein. The use of a mixture of bromine and chlorine in this bromination is particularly advantageous.

When the acid of formula I or I'' is one in which the aryl moiety contains a functional group which is itself reactive with the Grignard compound, it is usually necessary that this functional group be protected before the Grignard compound is formed. Operable protecting groups are well known in the art. The protecting group can later be removed, for example, by acidification.

It will be seen that when reacting an aryl magnesium bromide III or III'' with ethylene in the presence of a catalyst according to the invention, 2-aryl propionic acids are obtained therefrom by a more economical synthesis.

Additionally the present invention provides two improved coupling processes for the preparation of biaryl compounds having the formula

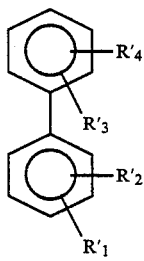

IV$_1$ wherein R'$_1$ and R'$_2$ are the same or different and are selected from the group consisting of hydrogen, halogen, alkoxy of from 1 to 6 carbons, inclusive, alkoxycarbonyl of from 1 to 4 carbons, inclusive, nitro, alkyl of from 1 to 4 carbons, inclusive, cycloalkyl of from 4 to 7 carbons, inclusive, phenyl, cyano and

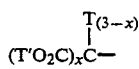

wherein X is an integer of one or two and T is hydrogen or alkyl of from 1 to 4 carbons, inclusive; T' is selected from the group consisting of alkyl of from 1 to 4 carbons, inclusive or two T' groups taken together which form a cyclic diester; and R'$_3$ and R'$_4$ are the same or different and are selected from the group consisting of hydrogen, hydroxyl, halogen, nitro, alkyl of from 1 to 4 carbons, inclusive, alkoxy of from 1 to 4 carbons, inclusive, alkoxycarbonyl having alkoxy of from 1 to 6 carbons, inclusive, aryloxycarbonyl, phenyl, cyano, and cycloalkyl of from 4 to 7 carbons, inclusive, which comprises coupling a compound selected from the group consisting of

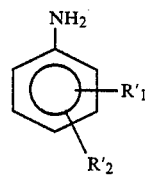

V$_1$ with a compound selected from the group consisting of

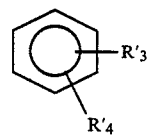

VI$_1$ wherein R'$_1$ through R'$_4$ are as defined above. In the preferred of the two improved coupling reactions, the compound V$_1$ is reacted with a metal nitrite in the presence of compound VI, and an acid in an aqueous or nonqueous medium. Especially preferred is the simultaneous addition of the compound V$_1$ and the acid to a mixture of metal nitrite and compound VI$_1$.

In the second coupling process of the invention an improved preparation of the above biaryl IV$_1$ is accomplished in a process which comprises coupling the compound V$_1$ with the compound VI$_1$ by separately and simultaneously adding the compound V$_1$ and an alkyl nitrite to the compound VI$_1$.

Cyclic diesters are 2,2-dialkyl-1,3-dioxane-4,6-dione in which alkyl is limited to from 1 to 4 carbons inclusive, 2,2-dimethyl-1,3-dioxane-4,6-dione is preferred.

The compounds included in the coupling process described above having only two substituents per phenyl ring in the biaryl product is not meant to be limiting.

The alkyl nitrite is an alkyl compound of from 1 to 6 carbons inclusive and includes methyl, ethyl, propyl, butyl, pentyl and hexyl and isomers thereof.

Preferred and especially preferred compounds prepared in the coupling processes include those used to prepare compounds I and II having the moieties noted therefore above, such as bromides from which the aryl magnesium bromides III can be prepared, for example 2-fluoro-4-biphenylyl bromide. Also especially preferred compounds prepared herein are biaryls having the formulas:

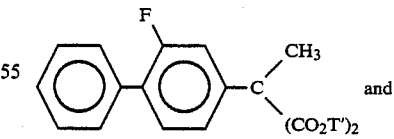 and

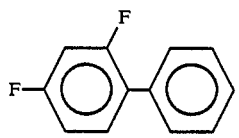

wherein T' is the same as above.

The above coupling processes unexpectedly improve the known Gomberg or Gomberg-Bachmann reaction discussed by March in Advanced Organic Chemistry:

Reactions, Mechanisms, and Structure, pages 550–551, 1968 (McGraw-Hill, Inc.). However, March noted that "yields are not high (usually under 40%) because of the many side reactions undergone by diazonium salts" which are described as intermediates therein. Cadogan in J. Chem. Soc., page 4257 (1962) discloses the use of pentyl nitrite as the diazotising agent with increasing yields of the named biaryls. Other more recent references, such as Meth. Appl. 6,500,865, 7/26/75; C.A. 64, 5005e (1966), and U.S. Pat. No. 3,992,459 disclose various coupling reactions, based on the Gomberg or Gomberg-Bachmann citations; however, none suggest the improvements of the present invention processes in which yields of biaryl compounds are unexpectedly increased.

Although again speculation herein about the mechanisms by which these two processes of the present invention provide improved yields is not meant to be controlling, it is believed that formation of intermediate diazonium salts are limited and therefore side reactions reducing yields in prior art processes are avoided. This rationale is supported by the discovery that the present processes provide an additional advantage in that no precautions are required to avoid explosive decomposition of diazonium salts while preparing and handling large amounts of reaction mixtures. Therefore the coupling processes of the invention are unexpectedly advantageous over the prior art teachings.

Among the arylpropionic acids which are the subject of this application is an important non-steroidal antiinflammatory agent known as flurbiproten or 2-(2-fluoro-4-biphenylyl)propionic acid. To use the processes which are the subject of this application to make flurbiprofen, 4-bromo-2-fluoroaniline is needed as the starting material; therefore there is also provided an improved preparation of 4-bromo-2-fluoroaniline which comprises reacting 2-fluoroaniline with a brominating agent, especially preferred dibromantin (1,3-dibromo-5,5-dimethylhydantoin) in a solvent comprising dimethylformamide or dimethylacetamide. Dibromantin in dimethylformamide unexpectedly provides nearly quantitative results with unusually high selectivity at the 4-position.

U.S. Pat. No. 3,987,057 shows that the bromination of 2-fluoroaniline is known to those skilled in the art, citing for example, J. B. Wommack et al., J. Het. Chem., 6, 243 (1969). The first report that 4-bromo-2-fluoroaniline is useful as a starting material appears in K. Kuroda et al., Nippon Kagaku Kaishi, 1876 (1973); Chem. Abstr., 78, 43571q (1973). However, these references fail to appreciate the improved preparation now provided by the present invention.

In view of the above novel preparations, a total process not hitherto suggested by the prior art for the preparation of arylpropionic acids is considered to be within this invention. That is the present invention provides a process for the preparation of a compound selected from the group consisting of

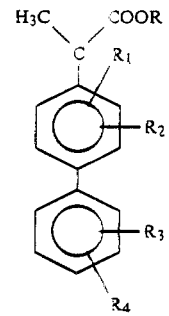

which comprises (i) coupling a compound selected from the group consisting of

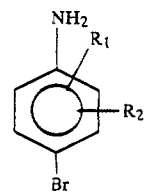

with a compound selected from the group consisting of

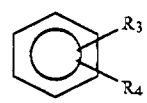

to prepare a compound selected from the group consisting of

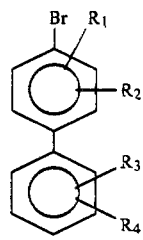

and (ii) preparing a compound selected from the group consisting of

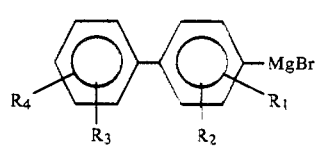

from the compound prepared in step (1);

(iii) preparing a compound selected from the group consisting of

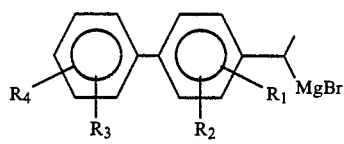
II' by reacting the compound III' of step (2) with ethylene in the presence of a catalyst; and (iv) carboxylating the compound II' to prepare the compound I' wherein $R_1$, $R_2$, $R_3$ and $R_4$ are all as defined above. Therefore the invention also includes preparations or improved preparations for compounds used in novel processes of the invention to make arylmagnesium bromides corresponding to the particular Grignard compounds made by the novel reaction with ethylene as described herein and from which preferred arylpropionic acids are derived.

It is also understood that the above step (i) coupling reaction is not limited to the novel process conditions of this invention. For example, conditions similar to those described in U.S. Pat. No. 3,992,459 may be used to react compounds $V_1'$ and $VI_1'$ above. These conditions include the use of copper or copper salt.

Of particular interest is Example 5 wherein 4-bromo-2-fluoroaniline is substituted for the corresponding reactant, 2,4-difluoroaniline. However, some disadvantages exist in the recovery of the copper and/or disposal thereof which distinguish the coupling reaction preparing $IV_1$ of this invention noted above from U.S. Pat. No. 3,992,459. On the other hand, each of the coupling reactions disclosed herein may be further modified by conducting the reaction in the presence of copper.

One such total process which produces an especially preferred compound as named above is shown by the following schematic:

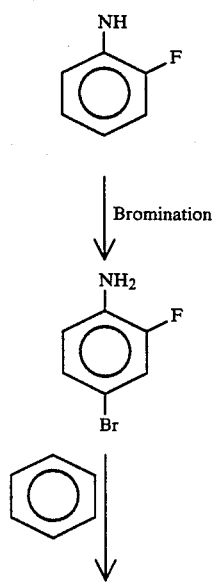

2-(2-fluoro-4-biphenylyl)propionic acid (flurbiprofen).

In addition to the advantages discussed previously for the reaction of arylmagnesium bromide, particularly 2-fluoro-4-biphenylyl magnesium bromide, with ethylene in the presence of a catalyst and unexpected increases in yields for the novel coupling reactions disclosed above there is also a noticeable economic advantage when making flurbiprofen using 2-fluoroaniline as a starting material in the total process of the invention.

Prior synthesis have utilized 2-amino-biphenyl compounds, which may be mutagenic. The present process avoids this type of intermediate.

With respect to the above novel processes for producing the compounds having Formula I or I" and Formula II or II", the following schematics are illustrative:

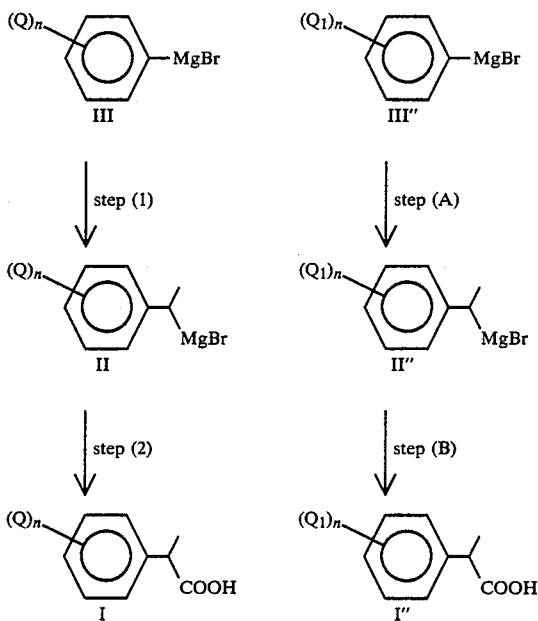

It is noted that U.S. Pat. No. 3,959,364 teaches a use for an aryl magnesium bromide similar to compounds III and III" of this invention, also in a process to make aryl propionic acids by reaction with a salt of 2-bromopropionic acid. However, the Grignard reaction disclosed therein does not have the advantageous yield and the desired use of less costly reactants as found in the present invention.

The steps 1 and A in which ethylene is reacted with a Grignard reagent are generally carried out in a conventional manner for Grignard reactions, e.g. in an anhydrous medium. The reaction is generally carried out at a temperature of 0° to the boiling point of the solvent. However, generally the Grignard reagent mixture is cooled to about −20° C. during addition of reactants and then allowed to warm to room temperature.

A catalyst is required to effect the reaction of ethylene with aryl Grignard reagent. It is disclosed that Ziegler-Natta type catalysts (when conditions are modified to inhibit polymerization) are efficaceous in this regard. Anhydrous salts of nickel are especially efficacious in the desired reaction. Although most nickel compounds will effect reaction to some extent, preferred nickel salts are nickel chloride or nickel bis(acetylacetonate).

It is further found that partial reduction of the nickel catalyst by pretreatment causes a surprising increase in the efficacy of the preferred nickel catalyst. Such a pretreated catalyst is especially preferred.

The pretreatment consists of the addition of from zero to 5 molar equivalents of an alkyl aluminum compound; for example, triisobutylaluminum, diethylaluminum chloride or bromide, triethylaluminum, ethylaluminum dichloride, to the nickel salt in an ether or tetrahydrofuran solvent under an inert atmosphere for 0.5 to 3 hours. Also effective conditions for pretreatment include the reaction of two molar equivalents of diisobutyl-aluminum hydride with anhydrous nickel bis(acetylacetonate) at −30° to 0° C. particularly in the above step 1 reaction.

Yields are greatly increased in both steps 1 and A by the evacuation of ethylene gas after absorption of the ethylene in the Grignard. The absorption is accomplished by saturation of the reagent mixture with the gas under three to four atmospheres of pressure with vigorous shaking or stirring and is complete when the reaction mixture shows no further absorption of ethylene.

Yields are also advantageously affected in both steps 1 and A by addition of ethylmagnesium bromide to the reaction mixture as described above, also after the mixture shows no further absorption of ethylene.

It is found in step 1 that absorption of ethylene occurs in an ether solvent such as di-n-butyl ether or diethyl ether, preferably diethyl ether. On the other hand, essentially no reaction occurs in a reaction mixture having tetrahydrofuran, methylene dichloride, 1,2-dimethoxyethane, or a mixture of equivalent amounts of diethylether and toluene as the solvent therefrom.

To the contrary, it is found that in step A, absorption of ethylene unexpectedly produces a high yield in an ether solvent, such as tetrahydrofuran, tetrahydropyran, 2-methyltetrahydrofuran, mixtures thereof or preferably one of these ethers in combination with a hydrocarbon cosolvent, such as toluene or hexane. In this reaction, on the other hand, only negligible yields are obtained in diethyl ether, dioxane, 2,5-dimethyltetrahydrofuran, di-n-butyl ether, diglyme, n-butyl ethyl ether, n-butyl methyl ether, dimethoxymethane, 2-methyltetrahydrofuran, or 4-methyldioxolane. Since 2-methyltetrahydrofuran is more expensive, the preferred ether component of the solvent system for this reaction is tetrahydrofuran.

However, it is particularly found that the use of the hydrocarbon cosolvent such as toluene or hexane advantageously reduces undesirable biproduct formation in the step A reaction. Effective ratios of ether to hydrocarbon in a solvent-cosolvent mixture range from 1:1 to 1:0. Use of the hydrocarbon cosolvent in step A causes an unexpected advantage by reducing the formation of dimers in the yield of the desired product II" and is therefore, preferred in a ratio by volume of from 1:1 to 3.5:2 with 1:1 especially preferred.

Reactions similar to those described above may be carried out in which the bromide in compounds III and III" are replaced by the equivalent chloro or iodo. Similar conditions are used with appropriate modifications depending on the reactants and corresponding products II and II" are carboxylated, acidified and recovered as I, and I" in a similar manner to that described hereinafter.

The mixture resulting from step 1 or step (A) is cooled, for carboxylation in step 2 or step (B) respectively, to between +10° C. and −30° C. It is then treated with dry carbon dioxide ($CO_2$) gas and thereafter acidified, for example with hydrochloric acid. A resulting organic phase is extracted with water and mild alkaline solutions, e.g., sodium or potassium bicarbonate. Compounds I or I" are isolated and purified from the combined aqueous extracts from the corresponding steps (2) or (B) above by conventional methods, e.g., extractions, evaporations, distillations, crystallizations, chromatography.

It is now also appreciated that a styrene-like compound IV and IV" can be reacted with an ethylmagnesium bromide under the corresponding optimum conditions previously described to obtain the desired angular Grignard reagent II and II" as follows:

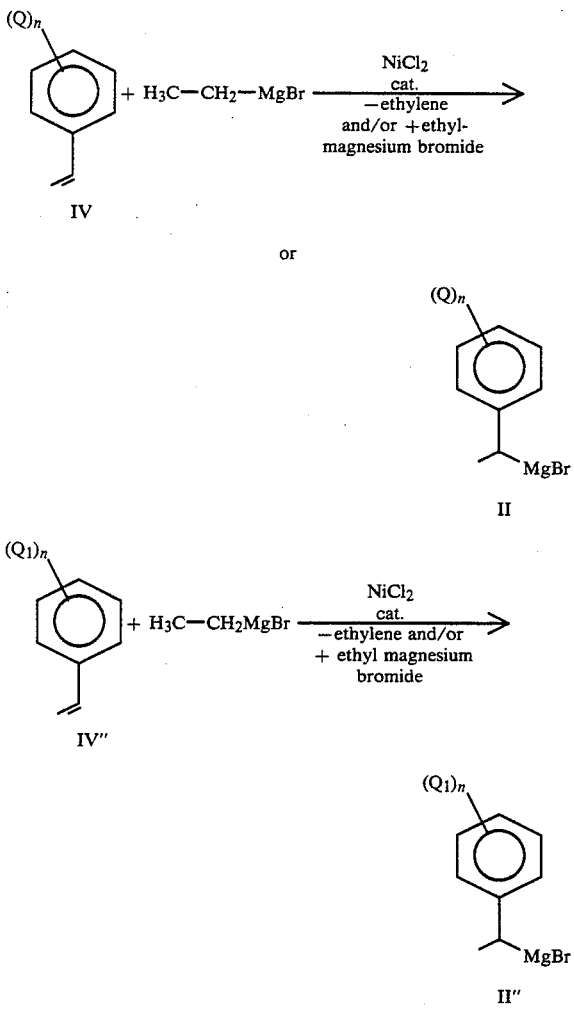

wherein n, Q and $Q_1$ are all as defined above.

Although Finkbeiner et al, cited above, discloses an exchange of olefins; e.g. styrene, with a Grignard reagent, it does not teach the novel process of this invention as shown above which react compounds IV and IV" with ethylmagnesium bromide in the presence of a nickel catalyst.

It is recognized that this reaction of compounds IV and IV" with ethyl magnesium bromide in the presence of a catalyst is generally carried out using the conditions described for steps 1 and A above, respectively.

The improved conditions of the coupling reactions in the invention as outlined above for the preparation of compound IV, are generally described in the following manner.

First, the preferred embodiment of the coupling reactions are as follows. A benzene solution of compound $V_1$ is added simultaneously with an acid to a nonaqueous mixture of excess compound $VI_1$ and solid sodium or potassium nitrite. Alternatively, a benzene solution of compound $V_1$ is added simultaneously with an acid to a mixture of excess compound $VI_1$ and an aqueous solution of sodium or potassium nitrite. The ratio of the amount of compounds $V_1$ to $VI_1$ ranges from 5:10 to 1:10. The acid may be a mineral acid such as sulfuric acid or an organic acid such as benzoic, chloroacetic, dichloroacetic, trichloroacetic, methanesulfonic or acetic acid. The temperature of the reaction mixture is maintained between 25° C. and the boiling temperature of the mixture. Temperatures in the higher end of the range are preferred. Molar amounts of acid and sodium or potassium nitrite to that of compound $V_1$ are each in the range of 1 to 4 times, preferably 2.5 times. In an especially preferred embodiment the compound $V_1$ and acetic acid are added dropwise to a mixture of the aqueous or nonaqueous metal nitrite in the compound $VI_1$. Stirring from 2 to 18 hours after the addition is completed at the preferred temperatures of the reaction is advantageous. The product $IV_1$, is isolated by cooling the reaction mixture, washing, evaporating, distilling, or other conventional procedures. A particularly simple and preferred workup is evaporation and extraction with hexane and washing with 85% sulfuric acid. Crude product $IV_1$ is obtained and further purification may not be necessary for use of the product in making the arylmagnesium bromide III to be reacted in the further novel processes of this invention. On the other hand, nitro compounds may be by-products in this reaction, so it is advantageous to reduce the reaction mixture by adding iron/acetic acid mixtures or sodium dithionite, which converts these by-products to amines, such that these can be removed from the product simply by washing with acid. Conditions for the reduction of nitro compounds are similar to those outlined by S. R. Faudler, et al., in "Organic Functional Group Preparations", Vol. 1, Academic Press, New York, 1968, p. 339.

If the coupling reaction is carried out in nonaqueous conditions with solid metal nitrite it is also advantageous to add an absorbent for water, such as anhydrous magnesium sulfate, silica gel or Celite ®. Furthermore, the use of potassium nitrite rather than sodium nitrite in this reaction gives a higher yield and is therefore among the preferred conditions for the anhydrous coupling reaction.

In addition to the above named acids for use in this reaction it is found that in the two phase aqueous reaction mixture hydrofluoric and fluoboric are effective. However, fluoboric acid ($HBF_4$) gives a particularly high and unexpected yield. If sulfuric acid is used a 10% solution is preferred.

In preparing the especially preferred 4-bromo-2-fluorobiphenyl compound IV for use in subsequent reactions according to the novel methods described herein the temperature of the coupling reaction is 25° to 80° C. and preferably 60° C.

The alternative coupling reaction, also noted above, employs alkyl nitrites instead of sodium nitrite and is accomplished in the absence of water. In this reaction a solution of the compound $V_1$ in excess benzene is reacted with alkyl nitrite such as isoamyl nitrite in the presence of the compound $VI_1$ at 20° to 80° C. over a period of 5 to 20 hours. Preferably in this embodiment of the invention, isoamyl nitrite and a solution of the compound $V_1$ in benzene are each added dropwise separately but simultaneously over a period of about 20 hours to an excess amount of the compound $VI_1$ while maintaining the temperature in the range of 25° C. to the boiling point of the solvent, preferably about 65° C. The product $IV_1$ is treated with a reducing agent and isolated in a manner analogous to that described above for the preferred coupling reaction using metal nitrite.

Finally, as noted earlier, each of the coupling reactions disclosed herein may be further modified by conducting the reaction in the presence of copper. For example, especially preferred is the use of the nonaqueous medium with sodium or potassium nitrite described herein with copper present. The copper may be in the form of a copper powder or a copper salt. However, if a copper powder is chosen, reaction conditions are used which assure a timely preparation of copper salt in situ. Prior art does not teach the combination of conditions as found in this invention using solid sodium or potassium nitrite in a nonaqueous acidic medium, also having copper present. Therefore, this particular coupling reaction is itself novel.

Bromination of 2-fluoroaniline described above is generally accomplished by dropwise addition of a solution of brominating agent to a solution of 2-fluoroaniline under conditions recited in J. B. Wommack, et al., J. Het. Chem., 6, 243 (1969) (see above). Temperatures of from 0° to −50° C., preferably from −23° C. to −34° C. are necessary to obtain the selective 4-position bromination with minimal formation of a dibrominated product. The brominating agent and solvent in the bromination of 2-fluoroaniline for use in the novel processes of the invention may be selected from among these known in the art. However, the preferred brominating agents are N-bromoamides or N-bromoimides with dibromantin noted above especially preferred. It is now found that the preferred solvents comprise dimethylformamide (DMF) and dimethylacetamide with DMF especially preferred. These preferred solvents provide unexpectedly large yields and unusually high selective bromination at the 4-position and therefore, provide an improvement not taught in the prior art. Various other solvents may be used such as formamide, N-methylformamide, dioxane, diglyme in ethylene chloride or benzene. The use of benzene has the advantage that the reaction mixture may be used in the coupling reaction described herein without further purification. Another possible advantageous variation is in situ preparation of the brominating agent, N-bromoacetamide in dimethylformamide.

The above especially preferred solvents also provide the named advantages in known corresponding chlorinations of 2-fluoroaniline.

The 4-bromo-2-fluoroaniline produced can be obtained from the reaction mixture by conventional means such as extraction, chromatography, distillation and combinations of these.

All temperatures are in degrees centigrade.
ml Is milliliters.
glc Is gas-liquid chromatography.
g-at Is gram atoms.

The following examples illustrate each novel aspect of this invention and at the same time demonstrate a total process for the preparation of 2-(2-fluoro-4-biphenylyl)propionic acid which is among the especially preferred compounds of the invention. However, this example should not be considered limiting as to the use of any particular part of the invention processes.

EXAMPLE 1

2-(2-fluoro-4-biphenylyl)propionic acid I'

A. 4-Bromo-2-fluoro-aniline V'

To 36.5 g (0.125 mole, based on assay of 97.7%) of 1,3-dibromo-5,5-dimethyl-hydantoin ("dibromantin") under nitrogen in a dropping funnel is added 37.5 ml of DMF. The mixture is stirred until the solids dissolve, and then the light yellow solution is added dropwise over 55 minutes to a solution of 24.1 ml of (0.250 mole) of 2-fluoroaniline in 30 ml of DMF, which is kept at −34° to −23° with a Dry Ice-acetone bath. The dropping funnel is rinsed with 5 ml. of methylene chloride, which was also added to the reaction. The reaction mixture is poured into a separatory funnel containing 27 ml of methylene chloride, 128 ml of heptane, 11 g of 50% NaOH, and 120 ml of water. After phase separation the aqueous layer is extracted with 50 ml of 20% methylene chloride in heptane, and the combined organic extracts are washed with 3×100 ml of water. Evaporation of the organic solution to constant weight gives 46.4 grams (98% of theory) of an oil. Glc analysis gave the following chemical yields: 4-bromo-2-fluoroaniline, 94%; 2-fluoroaniline, 0.2%, 2-bromo-6-fluoroaniline, 0.3%; 4,6-dibromo-2-fluoroaniline, 0%.

Instead of dibromantin, N-bromoamides or -imides, such as N-bromoacetamide or N-bromosuccinimide and other brominating agents can be used. Dibromantin is preferred.

B. 4-Bromo-2-fluorobiphenyl IV'.

(1) sodium nitrite procedure, with water.

A solution of 96 grams (0.50 mole) of crude 4-bromo-2-fluoroaniline and 60.0 grams (1.0 mole) of glacial acetic acid in 100 ml of benzene is added dropwise over 7 hours to a mixture of 69.0 grams (1.0 mole) of sodium nitrite, 69 ml water, and 700 ml of benzene kept at 65° C. The mixture is then allowed to stir at 65° C. overnight (12 hours) under a nitrogen atmosphere. The cooled mixture is washed twice with 400 ml of 1N hydrochloric acid, then heated under reflux overnight (13 hours) with 20 grams (0.36 mole) of iron powder, 250 ml of methanol, and 150 ml (1.8 moles) of concentrated hydrochloric acid. The resultant solution is cooled and the benzene layer is washed with 490 ml of water, and evaporated at 40° C./40 mm Hg. The resultant dark oil is distilled at 10 mm Hg pressure to obtain 64.6 grams (51.5%) of 4-bromo-2-fluorobiphenyl as the entire distillate of boiling point mostly ∼132∼141° C./8 mm. The product crystallizes on seeding.

Variations in the sodium nitrite procedure for the preparation of 4-bromo-2-fluorobiphenyl IV₁ give corresponding results as shown in Table I.

TABLE I

Ex. of compound: 4-bromo-2-fluoroaniline (NH$_a$, F, Br on benzene ring)

| Ex. | Br mmole | NaNO$_2$[1]/NO$_2$[2] mmole | H$_2$O ml | Acid mmole | Temp. °C. | Addn. Time hrs. | Yield % | Other mmoles |
| --- | --- | --- | --- | --- | --- | --- | --- | --- |
| (1)a | 50 | 125 [1] | 6.9 | 105 (acetic) | 60 | 3 | 55 | — |
| (1)b | 50 | 125 [1] | 6.9 | 105 (benzoic) | 60 | 2 | 52 | — |
| (1)c | 50 | 125 [1] | 6.9 | 100 (dichloroacetic) | 60 | 3 | 53 | — |
| (1)d | 50 | 125 [1] | None | 105 (acetic) | 60 | 3.5 | 53 | — |
| (1)e | 50 | 125 [1] | 6.9 | 100 (methane sulphonic) | 60 | 2 | 53 | 72 anhy. MgSO$_4$ |
| (1)f | 50 | 125 [2] | None | 100 (acetic) | 60 | 3 | 59 | 72 anhy. MgSO$_4$ |
| (1)g | 50 | 125 [1] | 6.9 | 100 (BF$_4$H) | 60 | 2 | 61 | — |
| (1)h | 50 | 100 | 6.9 | 40 (10% H$_2$SO$_4$) | 70 | 2.5 | 55 | — |
| (1)i | 50 | 79 [1] | None | 152 (trichloroacetic) | 5 to 13 | ½ hr. | 82 | 15 cu powder and 83 anhy. MgSO$_4$ |

(2) Isoamyl nitrite procedure.

Solutions of 375 ml (325 g, 2.8 moles) of isoamyl nitrite, and of 378 grams (2.0 moles) of crude 4-bromo-2-fluoroaniline in 250 ml benzene are added separately and simultaneously dropwise over about 20 hours to 3500 ml of benzene vigorously stirred under a nitrogen atmosphere, and kept in a water bath at 65° C. The mixture is kept overnight at 65° C., then cooled, washed twice with 250 ml of water and evaporated. The dark oily residue is dissolved in 750 ml methanol and 450 ml concentrated hydrochloric acid, and treated with 138 grams (2.1 moles) of granular zinc, added in small portions over about 6 hours. In order to complete this "reductive upgrading", the solution is treated with 54 grams (1.0 mole) of fine iron filings over 0.5 hours. Within one hour the color of the mixture is visibly lighter. The solution is diluted with one liter of water and one liter of Skellysolve B hexanes, and the liquids are decanted from the remaining metals. The aqueous phase is extracted twice with one liter of Skellysolve B hexanes and the one liter of water, one liter of 1N NaOH, and one liter of water. The solution is then passed through anhydrous sodium sulfate and evaporated to provide 389 grams of 4-bromo-2-fluorobiphenyl.

This is distilled under vacuum to obtain a fraction of 282 grams (56%) of 2-fluoro-4-bromobiphenyl, b.p. 137°–155° C./11 mm Hg which crystallizes on standing.

Variations in the alkyl nitrite procedure for the preparation of 4-bromo-2-fluoro-biphenyl IV$_1$ give the corresponding results as shown in Table II.

TABLE II

| Ex. | Br mmole | isoamyl nitrile mmole | H$_2$O ml | Acid mmole | Temp. °C. | Addn. time hrs. | Yield % | Other mmoles |
| --- | --- | --- | --- | --- | --- | --- | --- | --- |
| (2)a | 50 | 79 | none | 76 (trichloroacetic) | 3 to 18 | ¾ hr. | 87 | 15 Cu powder anhy. 83 MgSO$_4$ |
| (2)b | 50 | 79 | none | 76 (trichloroacetic) | 3 to 18 | ¾ hr. | 88 | 15 Cu powder no MgSO$_4$ |

C. 2-(2-fluoro-4-biphenylyl)propionic acid I'.

All operations conducted under nitrogen or a CH$_2$=CH$_2$ atmosphere in dry equipment.

To 12.2 grams (0.50 g-at.) of magnesium in 100 ml anhydrous ether is added dropwise 15.6 grams (0.083 mole) 1,2-dibromoethane. After the reaction subsides refluxing, there is added dropwise over 2 hours a solution of 104.4 grams (0.416 mole) of distilled 4-bromo-2-fluorobiphenyl in 300 ml of ether. The mixture is then refluxed for one hour to complete the preparation of the Grignard reagent. The mixture is cooled to −20° C., saturated with ethylene gas, and 1.08 grams (8.5 millimoles) of anhydrous nickel chloride (NiCl$_2$) is added and the mixture is allowed to warm to room temperature under an atmosphere of ethylene gas at a 3–4 atom pressure with vigorous shaking or stirring. After ½ to 2 hours at room temperature (gas-liquid chromatography shows no more change), excess ethylene is thoroughly removed from the system by alternately evacuating to 10" vacuum with vigorous shaking or stirring for two to six cycles. The mixture is then cooled to −10° C. and treated with CO$_2$ gas until there is no more exotherm. The mixture is warmed to room temperature and acidified with 150 ml 6N hydrochloric acid. The organic phase is washed twice with 100 ml water, then extracted with 4 portions of 100 ml 1N potassium bicarbonate solution. The combined aqueous extracts are washed four times with 50 ml of methylene chloride, and then acidified with 40 ml of concentrated hydrochloric acid. The product is twice extracted with 50 ml of methylene chloride, which is passed through anhydrous sodium sulfate and evaporated to give crystalline crude 2-(2-fluoro-4-biphenylyl)propionic acid I' (flurbiprofen) in 50–80% yield, based on starting biphenyl.

The material is recrystallized several times from 4 times its weight (in ml) of 10–25% ethyl acetate in Skellysolve B hexanes (or heptane), using 5 weight percent Pittsburgh Cal-carbon for decolorization in the last crystallization, to obtain flurbiprofen in 34–54% yield, based on the biphenyl of melting point 110°–114° C.

In a preferred procedure, the mixed catalyst for the above reaction, on a 60 mMole scale, is prepared by adding dropwise, 0.83 ml (1.2 mMoles) of a 25% solution of triethylaluminum in hexane to a suspension of 164 mg (0.60 mMole) of anhydrous nickel bis(acetylacetonate) in 2 ml of anhydrous diethylether in a bath at −14° to −35° under a nitrogen or ethylene atmosphere. The mixture is stirred at the same temperature for 2 hours, then added to the aryl Grignard solution at −20°, as described above. Ethylene uptake in this experiment is as rapid as the experiment using 3 mole percent nickel chloride, that is not treated to prior alkylaluminum reduction. The yield of flurbiprofen, as determined by glc assay, was 82% chemical.

EXAMPLE 2

2-(4-isobutylphenyl)propionic acid I''

A. p-Bromoisobutylbenzene

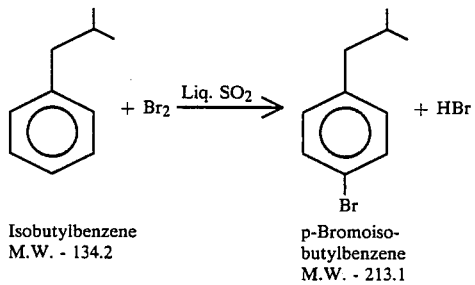

Isobutylbenzene
M.W. - 134.2 p-Bromoiso-
butylbenzene
M.W. - 213.1

Variation a without catalyst

To a solution of 67.1 grams (0.50 mole) of isobutylbenzene in 125 ml of liquid sulfur dioxide, under a nitrogen atmosphere, and cooled to −32° (−45° bath) is added over 13 minutes 95.9 grams (0.60 mole) of liquid bromine. The mixture is kept at about −33° C. for an hour, then treated with 25 ml of water and allowed to warm to room temperature, during which time sulfur dioxide and byproduct hydrogen bromide evaporated. The resultant organic phase is separated from the small aqueous phase. The aqueous phase is diluted with 75 ml of water and extracted with methylene chloride. The methylene chloride extract is combined with the original organic phase and washed with 25 ml of 20% sodium hydroxide solution and then twice with half-saturated sodium chloride solution. The organic solution is dried over anhydrous calcium chloride, then concentrated under vacuum to give 107.5 g of light yellow-colored oil.

Glc analysis of the product showed 1.4% starting isobutylbenzene, 5.1% o-bromoisobutylbenzene, and 94.0% p-bromoisobutylbenzene. This calculates out to a yield (% of theory) of 5% o-bromoisobutylbenzene and 95% p-bromoisobutylbenzene.

Variation b Using Iron Powder As Catalyst

This experiment is very similar to the uncatalyzed reaction, except that the reaction was run at −50° to −60° C. *after* preforming the catalyst at −7°.

Bromine (2 ml) is added to a slurry of 1.39 grams (0.025 grams-atoms, 5 mole-1%) iron powder in 125 ml of liquid sulfur dioxide kept at −7° C. After 0.5 hours at −7°, the mixture is cooled to −66° and the isobutylbenzene (67.1 grams, 0.5 mole) is added. The reaction mixture is kept at −52° to −60° during the addition of the remainder of a total of 101.9 grams (0.64 mole) of bromine during 6.5 minutes. The mixture is kept at −53° to 57° for 50 minutes, then treated with 49 ml of water and worked up essentially as in the above experiment A. The crude yield is 106.7 grams, which assayed 0.16 grams isobutylbenzene, 5.9 grams ortho-, and 91.3 grams para-bromoisobutylbenzene. This calculates out to a yield of 6% o-bromoisobutylbenzene and 93% p-bromoisobutylbenzene.

The major difference between this experiment and the preceeding one is the rate of bromination at the low temperature. Glc analysis of the reactions showed about 5% starting material after one hour reaction at −33° in the preceding reaction, but only 0.3% after one hour at −57° in the present one, indicating that preformed ferric bromide speeds the bromination at low temperatures.

Variation c Using Antimony Trichloride As Catalyst

A mixture of liquid sulfur dioxide (20 ml), antimony trichloride (149 milligrams, and bromine (0.52 ml, 1.52 grams, 9.5 milliMoles) at −30° C. is cooled to −72° (some solids) and treated in less than 3 seconds with 1.57 ml (10.0 milliMoles) of isobutylbenzene. The mixture, which contained considerable solids, is stirred at −69° to −72° for 70 minutes, at which point the reaction is quenched with 1.2 g (10.9 milliMoles) of resorcinol. The mixture is then warmed to room temperature (sulfur dioxide evaporated) and the product is extracted with hexane. The hexane solution is washed with aqueous sodium hydroxide and water, dried over anhydrous sodium sulfate, and diluted with hexane to a volume of 100 ml for glc analysis. Based on the assays, the yields are isobutylbenzene 16%, o-bromoisobutylbenzene 4%, and p-bromoisobutylbenzene 79%.

This and the following two experiments were competitive experiments, in an effort to determine relative reaction rates at 70° over 65–70 minutes. The reactions are quenched by adding resorcinol, which reacts almost instantly with the remaining bromine. A standard run without catalyst gave 22% isobutylbenzene, 2% ortho-, and 74% para-bromoisobutylbenzene. The higher conversion in the present experiment indicates that antimony trichloride increases the rate of the reaction.

Variation d Using Bromine Chloride As Brominating Agent

Bromine chloride (Dow, 1.12 g, 9.7 milliMoles) is condensed in a tube using Dry Ice cooling, then it is diluted with 20 ml of liquid sulfur dioxide and the resultant solution is cooled to −72° C. Isobutylbenzene (1.57 ml, 10.0 milliMoles) is added, and the resultant mixture is stirred at −70° for 65 minutes before quenched with 1.2 grams (10.9 milliMoles) of resorcinol. Workup and analysis as above gives 8% isobutylbenzene, 6% ortho-, and 83% para-bromoiso-butylbenzene. This result indicates that the bromination with bromine chloride is faster than that with molecular bromine, and the extent of ortho-bromination is somewhat higher.

A similar experiment, but in which the BrCl solution in liquid sulfur dioxide is added to the isobutylbenzene in liquid $SO_2$ at $-70°$, gives yields, respectively of 16%, 5%, and 80%.

Variation e Using N-bromosuccinimide

To a mixture of 1.78 g (10 milliMoles) of N-bromosuccinimide in 20 ml of liquid sulfur dioxide at $-30°$ C. is added 1.57 ml (10.0 mMoles) of isobutylbenzene. The mixture is stirred at $-30°$ to $-18°$ for 65 minutes, then worked up as above. Assay gives only 2% p-bromoisobutylbenzene and 88% recovered starting isobutylbenzene, indicating that the reaction with NBS is very slow at this temperature.

Variation f Using N-bromoacetamide Catalyzed by BrCl

To a mixture of 1.39 grams (10 milliMoles) of N-bromoacetamide in 19 ml of liquid sulfur dioxide at $-70°$ C. is added 1.57 ml (10.0 milliMoles) of isobutylbenzene. The mixture is treated with a solution of 0.05 ml of BrCl in 1.5 ml of $SO_2$ and then stirred at $-70°$ for 65 minutes, after which it is worked up as above. Glc analysis shows 62% isobutylbenzene, 1.5% ortho-bromoisobutylbenzene, and 35% para-bromoisobutylbenzene. This result shows that N-bromo compounds function as brominating agents if an acid catalyst (equivalent to HCl) is added. The low-temperature reaction in liquid $SO_2$ is catalyzed by iron powder or antimony trichloride, but these are not necessary for efficient bromination. Bromine chloride is also an effective catalyst to the brominating agent, giving as high as 90% conversion to the p-bromo isomer.

B. 2-(4-isobutylphenyl)propionic acid (ibuprofen)

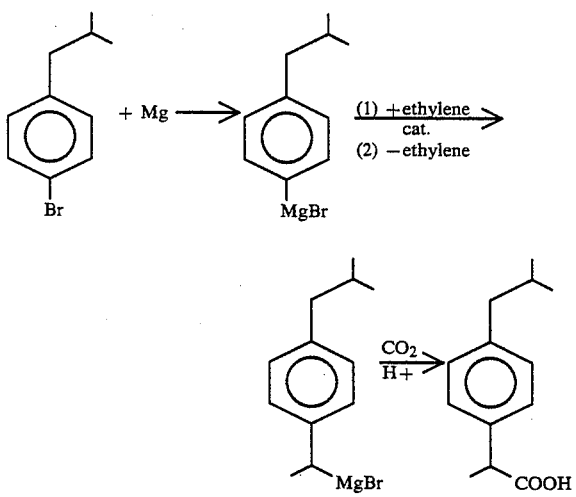

A solution of 1.0 ml of 1,2-dibromoethane in 10 milliliter of anhydrous tetrahydrofuran (THF) is added dropwise over 5 minutes to a mixture of 1.90 grams (78 grams atoms) of magnesium chips in 10 ml of THF. The mixture is refluxed for 2 minutes, then treated by dropwise addition, over 50 minutes, with a solution of 12.85 grams (60 mMoles) of p-bromoisobutylbenzene in 20 ml of THF. The resultant mixture is refluxed for 15 minutes to complete the reaction. The mixture is then cooled to $-20°$, 240 mg of anhydrous $NiCl_2$ is added, and the mixture is allowed to warm to room temperature, with vigorous stirring or shaking, under an atomsphere of ethylene gas at a pressure of 3–4 atmospheres. After 0.5 to 2 hours at up to 30°, the ethylene uptake ceases and the mixture is evacuated to $-10$ inches mercury, and shaken at this pressure for 20 minutes (bath temperature 45°) to completely remove excess ethylene from the solution. The mixture is then cooled to $-15°$ and treated with excess carbon dioxide gas. The product is isolated by acidification, extraction of the acidic product from ether with 1N potassium hydroxide, then acidification of the latter solution to obtain crude ibuprofen. Based on glc assay of the crude product, the chemical yield is 47%. Pure ibuprofen, m.p. 73°–74° is obtained with 91% recovery via recrystallization of the sodium salt from water, followed by acidification.

The wide range of hydratropic acids which can be prepared by the present invention are well known as therapeutic agents. For example, see Wong, "Chapter 18. Non-steroidal Anti-inflammatory Agents" *Annual Reports in Medicinal Chemistry Vol.* 10, *Utility of Hydratropic Acids,* Section IV—Metabolic Diseases and Endrocrine Function Ed: Morland pp. 172–181 (1975); U.S. Pat. Nos. 3,624,142; 3,755,427; 3,865,949; 3,784,705 and 4,052,514. Similarly, substituted biphenylyl compounds prepared by the novel coupling reaction of this invention are well known either as therapeutic agents or as precursors of therapeutic agents.

Starting materials used in the processes of this invention can be prepared by known methods, are known and/or are available commercially.

EXAMPLE 3

Alternate and Preferred Workup of Flurbiprofen by Distillation

A toluene extract of crude acids from hydrolysis and extraction of Grignard carboxylation, containing 51.3 g of flurbiprofen by glc assay, is evaporated, and the residue is distilled under vacuum. The fraction which boils at 119°–176° (mostly at 172°–176°) at a pressure of 0.4–0.5 mm is collected (49.2 g, which solidified) and recrystallized from a mixture of 25 ml of ethyl acetate and 170 ml heptane (decolorization with 0.5 g of Darco G-60). The dried product weighs 44.6 g (87% recovery of available product). Glc assay indicates a purity of 98.4%.

EXAMPLE 4

Bromination of 2-chloroaniline

A solution of 286 g (1.0 mole) of Dibromantin in 300 ml of DMF is added dropwise over 3 hours to a solution of 250 g (2.0 moles) of 2-chloroaniline in 235 ml of DMF, kept at $-30°$ to $-40°$ with a Dry Ice-acetone bath, and under a nitrogen atmosphere. The mixture is stored in the refrigerator at 0° overnight, then assayed for starting 2-chloroaniline by glc. Since there is a small amount of 2-chloroaniline left (approx. 2%), an additional 2.86 g (0.01 mole) of Dibromantin in 3 ml of DMF is added over 3 minutes to the reaction mixture cooled to $-25°$. The reaction is then warmed to 20° and diluted to exactly 1000 ml with DMF, in order to sample for glc analysis. Glc assay indicates the yield of 4-bromo-2-chloroaniline is 99%. The DMF solution is shaken in a separatory funnel with a mixture of 96 g (1.2 moles) of 50% sodium hydroxide solution, 1.25 liters of 20% methylene chloride in hexane solution, and 500 ml of water. The aqueous phase is extracted with 200 ml of 20% methylene chloride in hexane.

The organic phases are washed in succession with the same 500 ml aliquot of water, then combined and diluted with 300 ml methylene chloride when product begins to crystallize because of removal of DMF. The solution is washed with 500 ml water and then concentrated under vacuum to a thick slurry. This is diluted with 450 heptane, heated to dissolve the crystals, then allowed to cool with seeding to obtain a mixture of crystals and oil (because of the DMF). Hence the mixture is reheated, treated with 250 ml of water, cooled and seeded. The product crystallizes nicely from the two-phase system. It is washed with 300 ml water and 250 ml of −20° hexane and dried overnight at room temperature to obtain 367 g (91%) of 4-bromo-2-chloroaniline, m.p. 69°–71°.

EXAMPLE 5

4-Bromo-2-chlorobiphenyl

To a solution of 304 g (4.41 moles) of sodium nitrite and 244 ml of water in 2.5 liters of benzene, under a nitrogen atmosphere and in a water bath at 62°, is added dropwise over 8 hours a solution of 365 g (1.77 moles) of 4-bromo-2-chloroaniline and 212 ml (3.71 moles) of gl acetic acid in 212 ml of benzene. The dark mixture is stirred overnight. The lower aqueous layer is removed and benzene is distilled at atmospheric pressure. The residue is mixed with 600 ml methanol and 81.4 g of iron power, then 1.093 liters of concentrated hydrochloric acid is slowly added. The mixture is refluxed for 5.5 hours, then diluted with 1.4 l of hexane and 1.4 l of water and allowed to cool. The resultant slurry is filtered through Celite, which is rinsed well with hexane. The hexane phase is washed with water, dried over anhydrous magnesium sulfate, stirred with 40 g of Pittsburgh activated carbon, filtered again, and concentrated to constant weight (355 g). The Celite cake is extracted with acetone and treated separately.

The crude evaporated acetone extract is stirred with a mixture of 200 ml methylene chloride, 200 ml 85% sulfuric acid, and 300 ml hexane. The organic phase is washed with 3×200 ml of 85% sulfuric acid, each washing is back-extracted with the same 200 ml portion of hexane. The organic phases are finally washed with water and concentrated to obtain 28 g of oil containing a substantial amount of the product.

This is combined with the above 355 g crude product and chromatographed on 3 kg of silica gel with hexane. Fractions containing the product are collected, combined, and evaporated to constant weight to obtain a total of 292.9 g (62%) of 4-bromo-2-chlorobiphenyl as a colorless oil. Gc-ms (gas chromatography-mass spectrometry) confirmed the structure: the mass spectrum consists of a typical BrCl (bromochloride) triad at 266 (M+), 268 (base peak) and 270.

EXAMPLE 6

2-(2-Chloro-[1,1]-biphenyl-4-yl)propionic acid

To a slurry of 3.8 g (0.156 g-at) magnesium chips in 50 ml of anhydrous ether is added a solution of 2.1 ml (24 mmoles) of 1,2-dibromoethane, under a nitrogen atmosphere. When the reaction subsides there is added slowly over 2 hours, a solution of 32.4 g (121 mmoles) of 4-bromo-2-chlorobiphenyl in 40 ml of anhydrous ether. The reaction is kept near the boiling point during the addition, and is completed by refluxing the mixture for 15 minutes after the end of the addition. The mixture, in a Parr bottle, is cooled to < −20°, 470 mg of anhydrous nickel chloride is added, the bottle is placed in the Parr apparatus, and shaken under an atmosphere of ethylene gas at 60 psig. (pounds per square inch gauge). The mixture is shaken vigorously without heating for 15 minutes, by which time the temperature of the contents rise to 26°. Water is circulated in the jacket to maintain a temperature of 28°–30°. After a total of 38 minutes the uptake of ethylene ceases. Pressure is released, and the mixture is shaken, with occasional evacuation to maintain a pressure below atmospheric (1–8" vacuum) for about 0.5 hours. The mixture is then cooled to ∼ −13° by circulating −35° coolant in the jacket. The bottle is pressurized to 20 pounds per square inch gauge with dry carbon dioxide gas, and the mixture is shaken for about 0.5 hours, during which time the temperature rises to 20°.

Pressure is released, and the reaction mixture is acidified with excess 1N HCl. The ether layer is separated, washed with 2×25 ml of water, and extracted with sufficient 1M KOH to obtain a pH of 10 in the aqueous layer. The organic phase is extracted with 25 ml of water, and the combined aqueous phases are washed with 50 ml of ether. The aqueous extracts are acidified with excess 10% sulfuric acid and extracted with 150 and 25 ml portions of ether. The two ether extracts are combined, washed with 50 ml of water, and passed through a plug of cotton into a dry flask.

The ether solution is diluted to 250 ml with anhydrous ether and stirred under an ammonia atmosphere for 0.5 hours to precipitate the ammonium salt. After cooling the slurry in ice, the salt is collected, washed with ether, and dried in a stream of nitrogen to obtain 26.4 g (79%) of the ammonium salt as a granular off-white solid.

The ammonium salt is recrystallize from water containing a small amount of ammonia. The free acid, obtained on acidification of the ammonium salt, is recrystallized from heptane-ethyl acetate to give 18.4 g (58%) of "chlorobiprofen", m.p. 134°–6°.

EXAMPLE 7

4-Bromo-2-fluorobiphenyl

A slurry containing 1.0 grams (15 millimoles) copper powder, 12.5 grams (76.5 millimoles) trichloroacetic acid and 125 milliliters benzene is stirred at 23° to 26° C. under a nitrogen blanket for 4½ hours. The slurry is cooled to 6° C. and 10.5 milliliters (78.5 millimoles) isoamyl nitrite is added. After waiting 1½ minutes a solution containing 9.5 grams (50 millimoles) 4-bromo-2-fluoroaniline in 50 milliliters benzene is added dropwise over ½ hour to the slurry keeping the temperature of the slurry pot between 8° and 17° C. When the addition is complete the green slurry is allowed to warm to 25° C. and is stirred at 23° to 25° C. overnight.

Analysis by gas liquid chromatography shows a chemical yield of 88.7%.

I claim:

1. A process for the preparation of a compound selected from the group consisting of

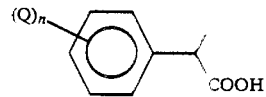

in which n is an integer of from 1 to 4, inclusive, and $Q_1$ is the same or different and is selected from the group consisting of aralkyl, cycloalkyl, alkyl substituted cycloalkyl, cycloalkenyl, aryl, alkoxy, aralkoxy, cycloalkoxy, aryloxy, alkylthio, aralkylthio, cycloalkylthio, arylthio, aryl(dialkoxy)methyl, aryl(alkylenedioxy)methyl, N-alkyl-N-arylamino, trifluoromethyl, fluorine and chlorine, dialkylamino, substituted and unsubstituted pyridyl, piperidyl, furyl, n-alkyl-morpholino, N-alkylthiamorpholino, pyrrolinyl, pyrrolidinyl, pyrrolyl, thienyl, or two Q groups taken together which form a heterocyclic ring, or Q such that together with

is 9H-carbazol-3-yl or substituted naphthyl, or naphthyl substituted on the 6-position by a moiety selected from the group consisting of alkyl, cycloalkyl, phenyl alkoxy, fluorine and chlorine, which comprises Step (1) preparing a compound selected from the group consisting of

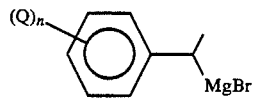 II by reacting a compound selected from the group consisting of

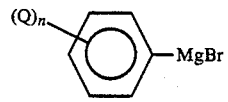 III with ethylene in the presence of an anhydrous nickel catalyst, selected from the group consisting of nickel chloride or nickel (bis)acetylacetonate, which nickel catalyst is pretreated with a reducing agent;

Step (2) carboxylating the Compound II prepared in Step 1 to obtain Compound I.

2. A process according to claim 1 wherein the reducing agent is an alkyl aluminum compound.

3. A process according to claim 2 wherein the alkyl aluminum compound is selected from the group consisting of triisobutylaluminum, diethylaluminum chloride, diethylaluminum bromide, triethylaluminum or ethylaluminum dichloride.

4. A process for the preparation of a compound selected from the group consisting of

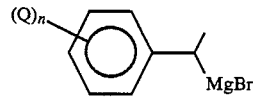 II where n is an integer of 1 to 4 and $Q_1$ is the same or different and is selected from the group consisting of aralkyl, cycloalkyl, alkyl substituted cycloalkyl, cycloalkenyl, aryl, alkoxy, aralkoxy, cycloalkoxy, aryloxy, alkylthio, aralkylthio, cycloalkylthio, arylthio, aryl(dialkoxymethyl), aryl(alkylene dioxymethyl), N-alkyl-N-arylamino, trifluoromethyl, fluorine and chlorine, dialkylamino, substituted and unsubstituted N-pyridyl, piperidyl, furyl, N-alkyl-morpholino, N-alkylthiamorpholino, pyrrolinyl, pyrrolidinyl, pyrrolyl, thienyl, two Q groups together from a heterocyclic ring or Q such that taken together with

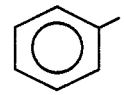

is 9H-carbazol-3-yl or substituted naphthyl which comprises reacting the compound selected from the group consisting of

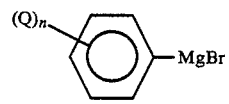 III with ethylene in the presence of an anhydrous nickel catalyst, selected from the group consisting of nickel chloride or nickel bis(acetylacetonate), which nickel catalyst is pretreated with a reducing agent.

5. A process according to claim 4 wherein the reducing agent is an alkyl aluminum compound.

6. A process according to claim 5 wherein the alkyl aluminum compound is selected from the group consisting of triisobutylaluminum, diethylaluminum chloride, diethylaluminum bromide, triethylaluminum or ethylaluminum dichloride.

7. A process for the preparation of a compound having the formula

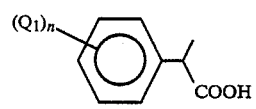 I'' wherein n is an integer of from 1 to 4, inclusive, and $Q_1$ is the same or different and is selected from the group consisting of alkyl of from one to four carbons, inclusive, cycloalkyl, alkyl substituted, cycloalkyl and cycloalkenyl, which comprises Step (1) preparing a compound selected from the group consisting of

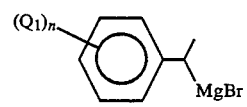 II'' by reacting a compound selected from the group consisting of

 III'' with ethylene, in a solvent selected from the group consisting of tetrahydrofuran, tetrahydropyran or 2-methyltetrahydrofuran or mixtures thereof, and in the presence of an anhydrous nickel catalyst selected from the group consisting of nickel chloride or nickel bis(acetylacetonate), which nickel catalyst is pretreated with a reducing agent; and Step (2) carboxylating the Compound II″ prepared in Step 1 to obtain Compound I″.

8. A process according to claim 7 wherein the reducing agent is an alkyl aluminum compound.

9. A process according to claim 8 wherein the alkyl aluminum compound is selected from the group consisting of triisobutylaluminum, diethylaluminum chloride, diethylaluminum bromide, triethylaluminum or ethylaluminum dichloride.

10. A process for the preparation of a compound having the formula

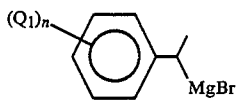
II″ wherein n is an integer of from 1 to 4, inclusive, and $Q_1$ is the same or different and is selected from the group consisting of alkyl of from one to four carbons, inclusive, cycloalkyl, alkyl substituted, cycloalkyl and cycloalkenyl, which comprises reacting a compound selected from the group consisting of

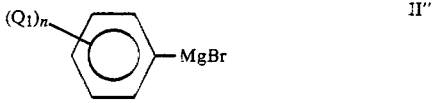
II″ with ethylene, in a solvent selected from the group consisting of tetrahydrofuran, tetrahydropyran or 2-methyltetrahydrofuran or mixtures thereof, in the presence of an anhydrous nickel catalyst selected from the group consisting of nickel chloride, nickel bis(acetylacetonate) and nickel bromide, which nickel catalyst is pretreated with a reducing agent.

11. A process according to claim 10 wherein the reducing agent is an alkyl aluminum compound.

12. A process according to claim 11 wherein the triisobutylaluminum, diethylaluminum chloride, diethylaluminum bromide, triethylaluminum or ethylaluminum dichloride.

* * * * *

UNITED STATES PATENT OFFICE
CERTIFICATE OF CORRECTION

Patent No. 4,518,799                          Dated 21 May 1985

Inventor(s) Thomas A. Hylton

It is certified that error appears in the above-identified patent and that said Letters Patent are hereby corrected as shown below:

Column 6, line 23: should read -- column $VI_1$ --.

Column 7, line 36: should read -- flurbiprofen --.

Column 15, line 32: should read -- those known --.

Column 17 (Table I formula): should read -- $NH_2$ --.

Column 18, (Table II formula): should read -- $NH_2$ --.

Column 24, line 37: should read -- recrystallized --.

Column 26, lines 4-5 (Claim 4): should read -- two O groups together form --

Column 28, lines 19-22 (Claim 12): should read -- A process according to claim 11 wherein the alkyl aluminum compound is selected from the group consisting of triisobutylaluminum, diethylaluminum chloride, diethylaluminum bromide, triethylaluminum or ethylaluminum dichloride. --.

Signed and Sealed this

Twenty-eighth Day of April, 1987

Attest:

DONALD J. QUIGG

Attesting Officer           Commissioner of Patents and Trademarks